US008689425B2

(12) United States Patent
Mutchler et al.

(10) Patent No.: US 8,689,425 B2

(45) Date of Patent: Apr. 8, 2014

(54) MANUFACTURING A SHOULDER PROSTHESIS WITH A ONE-PIECE HUMERAL HEAD

(75) Inventors: Austin W. Mutchler, Warsaw, IN (US); R. Sean Churchill, Mequon, WI (US)

(73) Assignee: Tornier, Inc., Edina, MN (US)

( * ) Notice: Subject to any disclaimer, the term of this patent is extended or adjusted under 35 U.S.C. 154(b) by 0 days.

(21) Appl. No.: 13/559,336

(22) Filed: Jul. 26, 2012

(65) Prior Publication Data

US 2012/0290098 A1 Nov. 15, 2012

Related U.S. Application Data

(62) Division of application No. 11/688,309, filed on Mar. 20, 2007, now Pat. No. 8,231,684.

(51) Int. Cl.
*B21D 39/00* (2006.01)
*A61F 2/40* (2006.01)

(52) U.S. Cl.
USPC .................................... 29/525.01; 623/19.14

(58) Field of Classification Search
USPC .......................... 29/525.01; 623/19.11, 19.14
See application file for complete search history.

(56) References Cited

U.S. PATENT DOCUMENTS 5,037,440 A 8/1991 Koenig
5,314,479 A 5/1994 Rockwood, Jr. et al.
6,045,582 A 4/2000 Prybyla
6,508,840 B1 1/2003 Rockwood, Jr. et al.
6,620,197 B2 9/2003 Maroney et al.
6,863,690 B2 3/2005 Ball et al.
6,899,736 B1 5/2005 Rauscher et al.
6,986,790 B2 1/2006 Ball et al.
7,044,973 B2 5/2006 Rockwood, Jr. et al.
2005/0256584 A1 11/2005 Farrar
2006/0036328 A1 2/2006 Parrott et al.
2006/0069445 A1 3/2006 Ondrla et al.
2006/0276903 A1 12/2006 Maroney et al.
2008/0039949 A1 2/2008 Meesenburg et al.

FOREIGN PATENT DOCUMENTS

EP 0845250 A2 6/1998
WO 02047821 A2 6/2002
WO 2006060992 A1 6/2006

*Primary Examiner* — Jermie Cozart
(74) *Attorney, Agent, or Firm* — Faegre Baker Daniels LLP

(57) ABSTRACT

A humeral head augment device for use in a modular shoulder prosthesis. The humeral head augment device has an external bearing surface with at least one surface portion that includes a radius of curvature. The radius of curvature is configured to constrain translational movement of the implanted shoulder prosthesis when the humeral head augment device is positioned within the shoulder prosthesis. The humeral head augment device also includes a coupling mechanism designed to lock the humeral head augment device to either the stem or the humeral head, thereby ensuring proper operational positioning of the device within the shoulder prosthesis and allowing the implanted shoulder prosthesis to function in a patient suffering from rotator cuff arthropathy. A shoulder prosthesis using a humeral head augment device, a method for assembling a shoulder prosthesis and method for using a humeral head augment device in a shoulder prosthesis are also disclosed.

6 Claims, 10 Drawing Sheets

MANUFACTURING A SHOULDER PROSTHESIS WITH A ONE-PIECE HUMERAL HEAD

CROSS-REFERENCE TO RELATED APPLICATIONS

This application is a divisional application of U.S. patent application Ser. No. 11/688,309 filed on Mar. 20, 2007, which issued on Jul. 31, 2012 as U.S. Pat. No. 8,231,684, the entire disclosure of which is incorporated herein by reference.

TECHNICAL FIELD

The present invention relates generally to orthopaedic implants. More particularly, the present invention relates to a shoulder replacement prosthesis and the method of use for treating rotator cuff arthropathy.

BACKGROUND OF THE INVENTION

Deterioration of an individual's rotator cuff may lead to the need to undergo a shoulder arthroplasty procedure. In severe cases, a person's humeral head may translate in a more superior direction during abduction of their effected arm resulting in the superior surface of the humeral head articulating with both the inferior surface of the acromion and the acromioclavicular joint. Articulation between these two bones could lead to accelerated destruction of the humeral head and erosion of the acromion and the acromioclavicular joint.

It was generally accepted practice for orthopedic surgeons to treat individuals with compromised rotator cuffs using standard sized shoulder stem prosthesis with oversized humeral heads to reestablish the joint space created by the bone loss. Humeral head bipolar prostheses have also been utilized by surgeons to address the stability problems associated with rotator cuff tear arthropathy. Both of these treatment modalities led to the overstuffing of the joint space and a resultant reduced range of motion for the effected arm of the individual. Several non-implant surgical techniques have been used with limited success in an attempt to address the rotator cuff tear arthropathy, including surgically smoothing the greater tubercle. Unfortunately, the individual still experienced reduced range of motion and joint pain because of the bone on bone contact.

Recent developments in the shoulder arthroplasty field involve the design of modular humeral heads that are configured to include a glenoid bearing portion and an extended acromion bearing portion. Problems that have been seen with these types of designs is excessive post-operative translation in the superior direction because of the previous bone loss and the use of a single radius of curvature for the two bearing portions. Another problem encountered with the extended bearing modular humeral heads is the head being incorrectly rotated when the prosthesis is assembled in the operating room. The malrotation may cause the humeral head to be positioned in a less then optimal location relative to the acromion during arm abduction.

SUMMARY OF THE INVENTION

Advancement of the state of orthopaedic implants and the treatment of rotator cuff tear arthropathy is believed desirable. The present invention satisfies the need for improvements to the shoulder replacement implant used to treat patients suffering from a torn rotator cuff or other soft tissue injuries by providing a modular humeral head augment device for coupling to a shoulder prosthesis.

The present disclosure provides in one aspect, a method of using a shoulder prosthesis. In some such embodiments, the method comprises obtaining at least one one-piece humeral head, the at least one one-piece humeral head having an external articulation surface portion with a radius of curvature, an external bearing surface portion with at least two radii of curvature, and an interior surface with a first connector extending therefrom. In some such embodiments, the method further comprises obtaining at least one stem, the at least one stem comprising a shaft, a proximal end, and a distal end defining a longitudinal axis therebetween, the proximal end having a second connector. In some such embodiments, the method further comprises engaging the first connector of the at least one one-piece humeral head to the second connector of the at least one stem to assemble the shoulder prosthesis such that the radius of curvature of the external articulation surface portion extends at least across the longitudinal axis of the stem. In some such embodiments, the external bearing surface portion of the at least one one-piece humeral head may comprise at least a first bearing surface portion of a first radius of curvature and a second bearing surface portion of a second radius of curvature that is different from the first radius of curvature, the first bearing surface portion being positioned adjacent the external articulation surface portion and the second bearing surface portion being positioned adjacent the first bearing surface portion. In some such embodiments, the first radius of curvature of the first bearing surface portion may be greater than the radius of curvature of the external articulation surface portion at least immediately adjacent the first bearing surface portion to constrain translation of the assembled shoulder prosthesis when implanted.

In some such embodiments, the method further comprises implanting the assembled shoulder prosthesis into a humerus of a recipient such that when in an operable position, at least the first bearing surface portion constrains translational movement of the implanted assembled shoulder prosthesis. In some such embodiments, the at least the first bearing surface portion constrains superior translation of the implanted assembled shoulder prosthesis during abduction of the recipient's arm.

In some embodiments, the first radius of curvature of the first bearing surface portion of the at least one one-piece humeral head may be greater than the second radius of curvature of the second bearing surface portion of the at least one one-piece humeral head. In some embodiments, the second radius of curvature of the second bearing surface portion of the at least one one-piece humeral head may be greater than the first radius of curvature of the first bearing surface portion of the at least one one-piece humeral head to further constrain translation of the implanted assembled shoulder prosthesis. In some embodiments, the external bearing surface portion of the at least one one-piece humeral head may define a medial side, a lateral side and a posterior side, and a relief may be disposed on the posterior side and extend at least one of from the medial side to the lateral side, from the medial side to a location intermediate the lateral side and medial side, and from the lateral side to a location intermediate the lateral side and medial side, thereby providing a space for passage of a posterior positioned soft tissue structure when the assembled shoulder prosthesis is implanted.

In some embodiments, the external bearing surface portion of the at least one one-piece humeral head may comprises at least one hole disposed therein, thereby allowing securement of a soft tissue structure to the at least one one-piece humeral head when the assembled shoulder prosthesis is implanted. In some embodiments, the radius of curvature of the external articulation surface portion extends to an angle of at least 180 degrees. In some embodiments, the radius of curvature of the external articulation surface portion extends from a side of the humeral head.

In some embodiments, the external articulation surface portion may encompass the entire exterior articulation surface of the at least one one-piece humeral head, and the combination of the first bearing surface portion and the second bearing surface portion may encompass the entire external bearing surface of the at least one one-piece humeral head. In some embodiments, when the assembled shoulder prosthesis is implanted in a recipient, the external articulation surface portion of the at least one one-piece humeral head may articulate with a first shoulder structure of the recipient's shoulder, and the first bearing surface portion of the at least one one-piece may bear against a second shoulder structure of the recipient's shoulder that is different from the first shoulder structure during abduction of the recipient's arm to constrain superior translational movement of the assembled shoulder prosthesis and thereby the recipient's arm.

The present disclosure provides in another aspect, a method of providing a shoulder prosthesis. In some such embodiments, the method comprises providing a one one-piece humeral head, the at least one one-piece humeral head having an external articulation surface portion with a radius of curvature, an external bearing surface portion with at least two radii of curvature, and an interior surface with a first connector. In some such embodiments, the further method comprises providing at least one stem, the at least one stem comprising a shaft, a proximal end, and a distal end defining a longitudinal axis therebetween, the proximal end having a second connector configured to engage the first connector of the at least one one-piece humeral head to assemble the shoulder prosthesis. In some such embodiments, the shoulder prosthesis may be configured such that the radius of curvature of the external articulation surface portion extends at least across the longitudinal axis of the stem when the shoulder prosthesis is assembled. In some such embodiments, the external bearing surface portion of the at least one one-piece humeral head may comprise at least a first bearing surface portion of a first radius of curvature and a second bearing surface portion of a second radius of curvature that is different from the first radius of curvature, the first bearing surface portion being positioned adjacent the external articulation surface portion and the second bearing surface portion being positioned adjacent the first bearing surface portion. In some such embodiments, the first radius of curvature of the first bearing surface portion may be greater than the radius of curvature of the external articulation surface portion at least immediately adjacent the first bearing surface portion to constrain translation of the shoulder prosthesis when assembled and implanted.

In some embodiments, the method further comprises engaging the first connector of the at least one one-piece humeral head to the second connector of the at least one stem to assemble the shoulder prosthesis. In some such embodiments, the method further comprises implanting the assembled shoulder prosthesis into a humerus of a recipient such that when in an operable position, at least the first bearing surface portion constrains superior translational movement of the implanted shoulder prosthesis during abduction of the recipient's arm.

In some embodiments, the first radius of curvature of the first bearing surface portion of the at least one one-piece humeral head may be greater than the second radius of curvature of the second bearing surface portion of the at least one one-piece humeral head. In some embodiments, the second radius of curvature of the second bearing surface portion of the at least one one-piece humeral head may be greater than the first radius of curvature of the first bearing surface portion of the at least one one-piece humeral head to further constrain translation of the implanted shoulder prosthesis. In some embodiments, the radius of curvature of the external articulation surface portion may extend to an angle of at least 180 degrees and from a side of the humeral head. In some embodiments, the external articulation surface portion may encompass the entire exterior articulation surface of the at least one one-piece humeral head, and the combination of the first bearing surface portion and the second bearing surface portion may encompass the entire external bearing surface of the at least one one-piece humeral head.

The present disclosure provides in another aspect, a method of manufacturing a shoulder prosthesis. In some such embodiments, the method comprises forming at least one one-piece humeral head, the at least one one-piece humeral head comprising an external articulation surface portion with a radius of curvature, an outer bearing surface portion with at least two radii of curvature, and an inner surface with a first connector extending therefrom. In some such embodiments, the method further comprises forming at least one stem, the at least one stem comprising a shaft, a proximal end, and a distal end defining a longitudinal axis therebetween, the proximal end having a second connector configured to engage the first connector of the at least one one-piece humeral head to assemble the shoulder prosthesis. In some such embodiments, the shoulder prosthesis may be configured such that the radius of curvature of the external articulation surface portion extends at least across the longitudinal axis of the stem when the shoulder prosthesis is assembled. In some such embodiments, the outer bearing surface portion of the at least one one-piece humeral head may comprise at least a first bearing surface portion of a first radius of curvature and a second bearing surface portion of a second radius of curvature that is different from the first radius of curvature, the first bearing surface portion being positioned adjacent the external articulation surface portion and the second bearing surface portion being positioned adjacent the first bearing surface portion. In some such embodiments, the first radius of curvature of the first bearing surface portion may be greater than the radius of curvature of the external articulation surface portion at least immediately adjacent the first bearing surface portion to constrain translation of the shoulder prosthesis when assembled and implanted.

In some embodiments, the method further comprises engaging the first connector of the at least one one-piece humeral head to the second connector of the at least one stem to assemble the shoulder prosthesis. In some embodiments, the first radius of curvature of the first bearing surface portion of the at least one one-piece humeral head may be greater than the second radius of curvature of the second bearing surface portion of the at least one one-piece humeral head. In some embodiments, the second radius of curvature of the second bearing surface portion of the at least one one-piece humeral head may be greater than the first radius of curvature of the first bearing surface portion of the at least one one-piece humeral head to further constrain translation of the shoulder prosthesis when assembled and implanted. In some embodiments, the radius of curvature of the external articulation surface portion may extend to an angle of at least 180 degrees and from a side of the humeral head. In some embodiments, the external articulation surface portion may encompass the entire exterior articulation surface of the at least one one-piece humeral head, and the combination of the first bearing surface portion and the second bearing surface may encompass the entire external bearing surface of the at least one one-piece humeral head.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features and advantages of the invention are apparent from the following detailed description taken in conjunction with the accompanying drawings in which:

BEST MODE FOR CARRYING OUT THE INVENTION

Generally stated, disclosed herein is a humeral head augment device and a shoulder prosthesis that includes as a component, a humeral head augment device. Further, described herein is a method for using a humeral head augment device with a shoulder prosthesis that may limit post-operative translateral movement for patients suffering from rotator cuff arthopathy.

Figure 1:
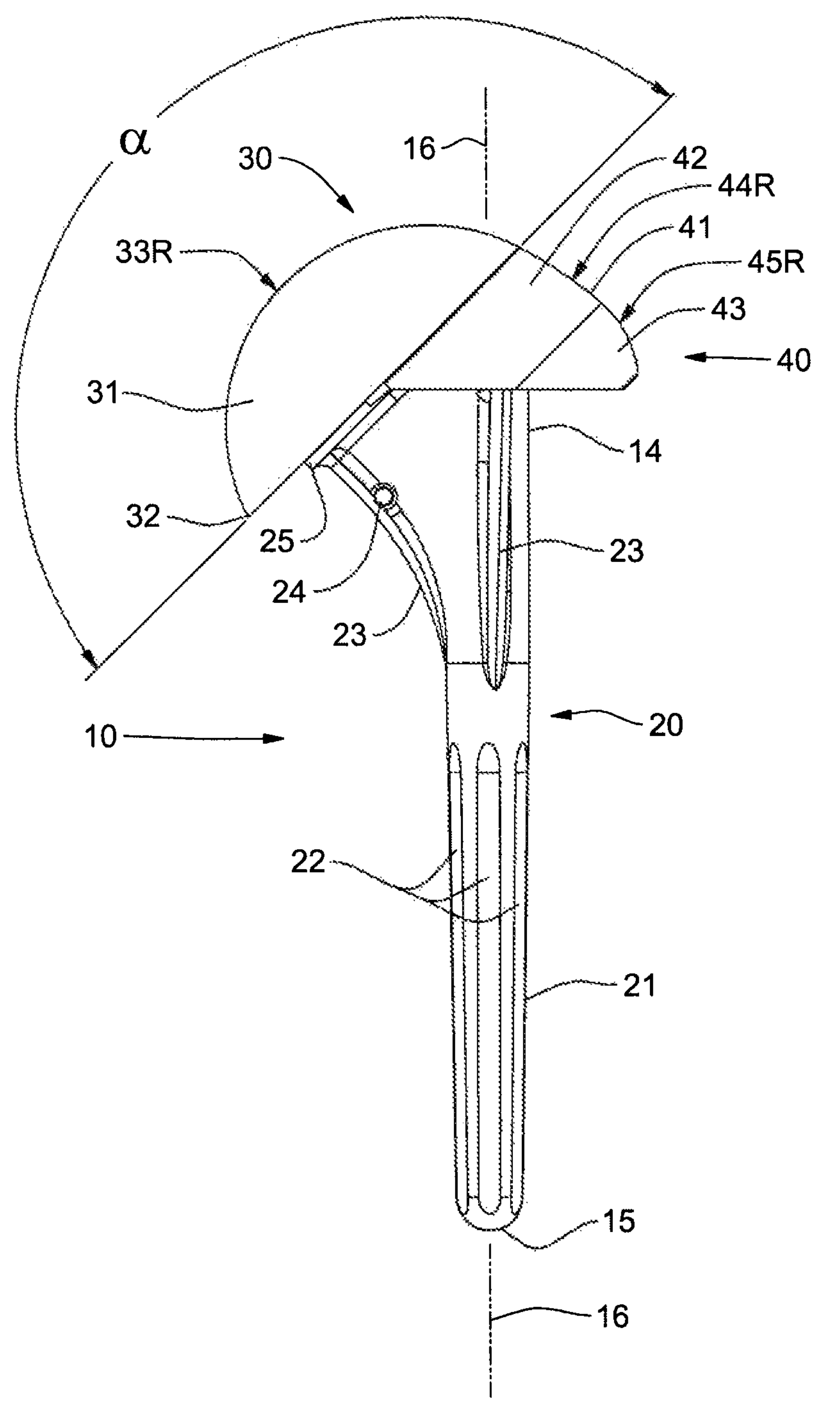
FIG. 1 is a side elevational view of one embodiment of a shoulder prosthesis with a humeral head augment device in operable position, in accordance with an aspect of the present invention.
Figure 2:
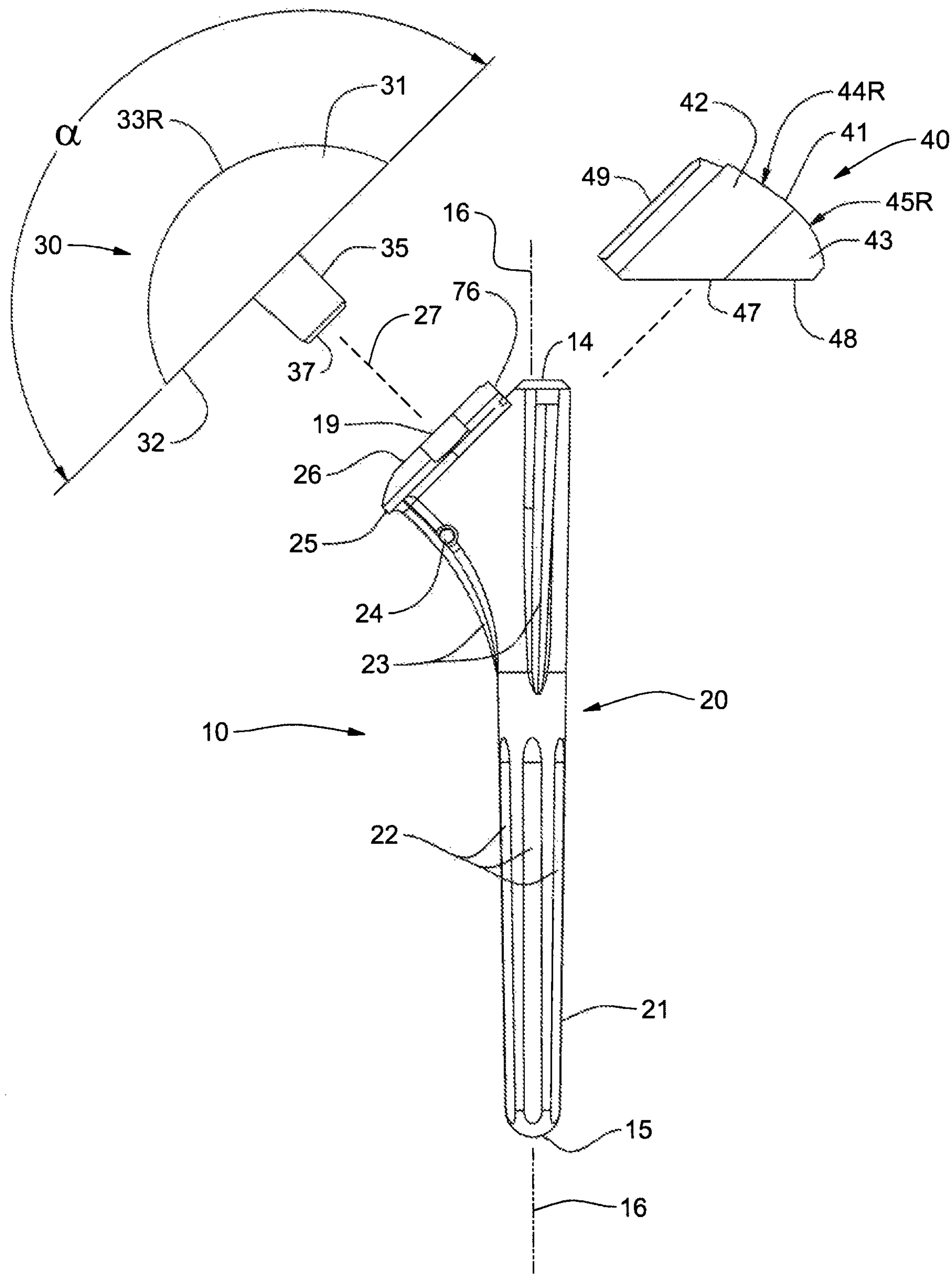
FIG. 2 is a side elevational, exploded view of the shoulder prosthesis with humeral head augment device of FIG. 1, in accordance with an aspect of the present invention.

As depicted in FIGS. 1 and 2, the general arrangement of a shoulder prosthesis 10 for use with a humeral head augment device 40, in accordance with an aspect of the present invention, includes a humeral head 30, a stem 20 and a humeral head augment device 40. In this detailed description and the following claims, the words proximal, distal, anterior, posterior, medial and lateral are defined by their standard usage for indicating a particular part of a bone or prosthesis according to the relative disposition of the natural bone or directional terms of reference. For example, "proximal" means the portion of a prosthesis nearest the torso, while "distal" indicates the portion of the prosthesis farthest from the torso. As for directional terms, "anterior" is a direction towards the front side of the body, "posterior" means a direction towards the back side of the body, "medial" means towards the midline of the body and "lateral" is a direction towards the sides or away from the midline of the body.

Figure 3:
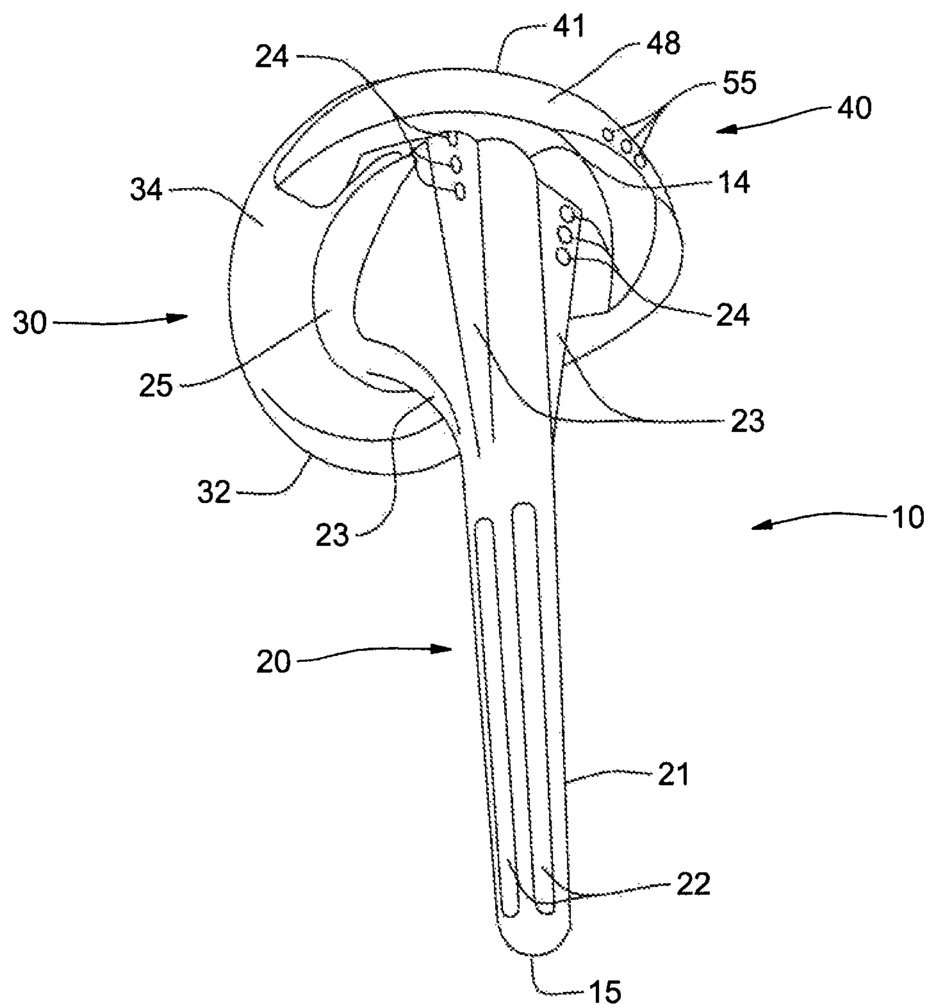
FIG. 3 is distal perspective view of the shoulder prosthesis with humeral head augment device of FIG. 1, in accordance with an aspect of the present invention.

With reference to FIGS. 1 and 2, stem 20 includes a proximal end 14, a distal end 15 and a longitudinal axis 16. A taper cavity 17 (see FIGS. 7A-E) is located on the medial side of proximal end 14 of stem 20. As shown in FIGS. 7A-E, taper cavity 17 is defined by a female taper 18 with a center axis 27 which is angled relative to longitudinal axis 16. Female taper 18 is configured to decrease radially when moving from the medial opening 19 of taper cavity 17 to the taper cavity bottom 28. Although not shown, it is contemplated that proximal end 14 may include a tapered post as an alternative to taper cavity 17, with both taper embodiments functioning to connect stem 20 to humeral head 30. As shown in FIGS. 3, 5A, 5B, 5C, and 6, proximal end 14 of stem 20 typically includes stability fins 23 located generally along the medial, anterior and posterior sides. Fins 23 may be straight or tapered and include numerous through holes 24 for fixation purposes. Positioned adjacent to medial opening 19 of taper cavity 17 is a support collar 25. The plane in which the proximal surface 26 of collar 25 lies is substantially normal to taper center axis 27. Collar 25 typically functions to provide support for stem 20 against the resected proximal surface of a patient's humerus. Additional functionality of collar 25 may include supporting humeral head 30 and provide motion control of humeral head augment device 40. As seen in FIG. 3, the shape of collar 25 may be designed to match the dimensions of the resected proximal humerus. It is contemplated that collar 25 may also have a circular, oval or oblong shape. It is not shown, but should be understood that proximal end 14 of stem 20 may not include collar 25 or alternatively, collar 25 may be modular, thereby allowing the operating surgeon at the time of implantation of shoulder prosthesis 10 to either attach or remove collar 25.

The distal shaft 21 of stem 20 may be integral to proximal end 14 or modular in design, allowing for a plurality of distal shafts 21 that are configured with varying lengths and diameters to be attached. Distal shaft 21 may include an assortment of bone or cement fixation mechanisms 22 along the outer surface of distal shaft 21. These may include, but are not limited to fins, flat surfaces, channels and cavities. Although not shown, distal shaft 21 may be coated with promoters of bone in-growth, including but not limited to porous coating, TCP, HA, metal mesh or other surface treatment sprays. The cross-section of distal shaft 21 is generally circular, although other shaped cross-sections are contemplated including, but not limited to hexagonal, trapezoidal, oval or polygonal.

As seen in FIGS. 1 and 2, humeral head 30 of shoulder prosthesis 10 includes an outer articulation surface 31. Articulation surface 31 has a substantially spherical contour that is typically comprised of one radius of curvature 33R, though multiple radius of curvatures may be incorporated into articulation surface 31 and are contemplated for treatment of unique clinical situations. As shown in FIGS. 1 and 2, preferably, articulation surface 31 extends to an angle $\alpha$ that is about 180 degrees. It is contemplated that angle $\alpha$ may be less than 180 degrees or greater than 180 degrees depending upon a patient's anatomical features and clinical application. Articulation surface 31 terminates at the intersection with an underside skirt 32 that is positioned around the full circumference of humeral head 30. Although not shown, at least one hole may be positioned proximate to skirt 32, allowing for securement of soft tissue for joint stabilization purposes. Intersecting skirt 32 is a substantially planar interior surface 34 that is positioned essentially opposite articulation surface 31 (see FIGS. 7A-7E). Extending from interior surface 34 in substantially perpendicular direction is a second connector shaped as a tapered post 35. As illustrated in FIGS. 7A-7E, tapered post 35 is sized and dimensioned to decrease radially from the post base 36 to the post end 37. Tapered post 35 is located generally in the center of interior surface 34 and is positioned and designed to mate with taper cavity 17 of proximal end 14. Although not shown, is should be understood to those skilled in the art that tapered post 35 may be eccentrically located on interior surface 34 allowing the operating surgeon to rotate and orient humeral head 30 to provide for optimal post-operative joint stabilization. Further, it is also contemplated that interior surface 34 may include a tapered cavity as an alternative to taper post 35, with both taper embodiments functioning to connect humeral head 30 to stem 20. When connected to stem 20, interior surface 34 of humeral head 30 may abut or alternatively, be positioned proximate to collar 25 and augment device 40.

When properly coupled to stem 20 of an implanted shoulder prosthesis 10, the convex, generally spherical shape of articulation surface 31 is configured to articulate either with a glenoid implant or the patient's natural glenoid. Radius of curvature 33R of humeral head 30 may range in size from 15 mm to 45 mm, with a more detailed range being between 19 mm to 30 mm. Radius of curvature 33R is configured and dimensioned to and allow for three degrees of motion for an implanted shoulder prosthesis 10, including rotational movement and translational or sliding movement in the superior-inferior direction and anterior-posterior direction.

Figure 4:
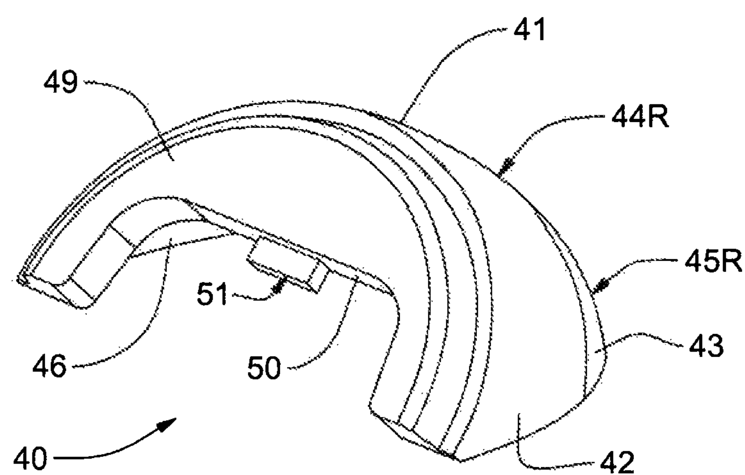
FIG. 4 is a perspective view of one embodiment of a humeral head augment device, in accordance with an aspect of the present invention.

As depicted in FIG. 4, humeral head augment device 40 includes a generally convex external bearing surface 41 that includes at least one radius of curvature that may be different than radius of curvature 33R of humeral head 30. External bearing surface 41 may be divided into two portions, the first portion 42 being located in the medial aspect of external bearing surface 41 and a second portion 43 being positioned in the lateral aspect of the external bearing surface 41. It should be understood to those skilled in the art that external bearing surface 41 may also be constructed of a single portion with a corresponding single radius of curvature for the entire external bearing surface 41. It should also be understood that external bearing surface 41 may further include greater than two portions with corresponding multiple radius of curvatures.

For example purposes, FIGS. 1 and 2 show that first portion 42 and second portion 43 have different radius of curvatures. The radius of curvature 44R of first portion 42 is usually greater than the radius of curvature 45R of second portion 43. The basis for the multiple radius of curvatures for external bearing surface 41 of humeral head augment device 40 is to limit or constrain the amount or degree of superior translation that may occur within implanted shoulder prosthesis 10 during abduction of a patient's arm. Radius of curvature 44R of first portion 42 may also be greater than radius of curvature 33R of articulation surface 31. Again, this geometric mismatch results in implanted shoulder prosthesis 10 being constrained from excessive superior translation when a patient's arm is taken through a full range of motion including abduction. Such constraint on superior movement is critical for patients suffering from deficient rotator cuffs caused by tears or soft tissue weakening and eroded bony structures, including the acromion and acromioclavicular joint. Humeral head augment device 40 may be modular in design, thus radius of curvatures 44R, 45R may have varying values ranging from 15 mm to infinity or be configured as a straight line segment. Mixing and matching values for radius of curvatures 44R, 45R as to each other and in combination with radius of curvature 33R allows the operating surgeon to optimize the desired shoulder joint range of motion provided by the implanted humeral head 30 in conjunction with humeral head augment device 40 with the presented anatomic structures of a patient. For example, it is contemplated that in some clinical cases radius of curvature 44R may be less than radius of curvature 45R and equal to radius of curvature 33R, thereby allowing more superior translation of shoulder prosthesis 10 during abduction. A further alternative may also be for humeral head augment device 40 to include only a single radius of curvature that is different than radius of curvature 33R of humeral head 30. For another clinical case it may be desirable for radius of curvatures 44R, 45R to be equal to each other, but greater than radius of curvature 33R, thus significantly restricting shoulder prosthesis 10 from any degree of superior translational movement. It should be understood to those skilled in the art that in yet another clinical case, it may be preferred that radius of curvatures 33R, 44R and 45R be equal to each other, thereby resulting in little or no geometric restriction of shoulder prosthesis 10 and a uniform and consistent radius of curvature for articulation surface 31 and external bearing surface 41.

FIG. 1 shows first portion 42 and second portion 43 being tangent to each other. This geometric relationship between first portion 42 and second portion 43 is essential to enable shoulder prosthesis 10 to move in a smooth and unrestricted or continuous manner while the patient's arm moves through a complete range of motion. Further, as seen in FIG. 1, articulation surface 31 is usually tangent to first portion 42, again to allow a patient to experience smooth and unrestricted or continuous movement of their implanted shoulder prosthesis 10.

Figure 6:
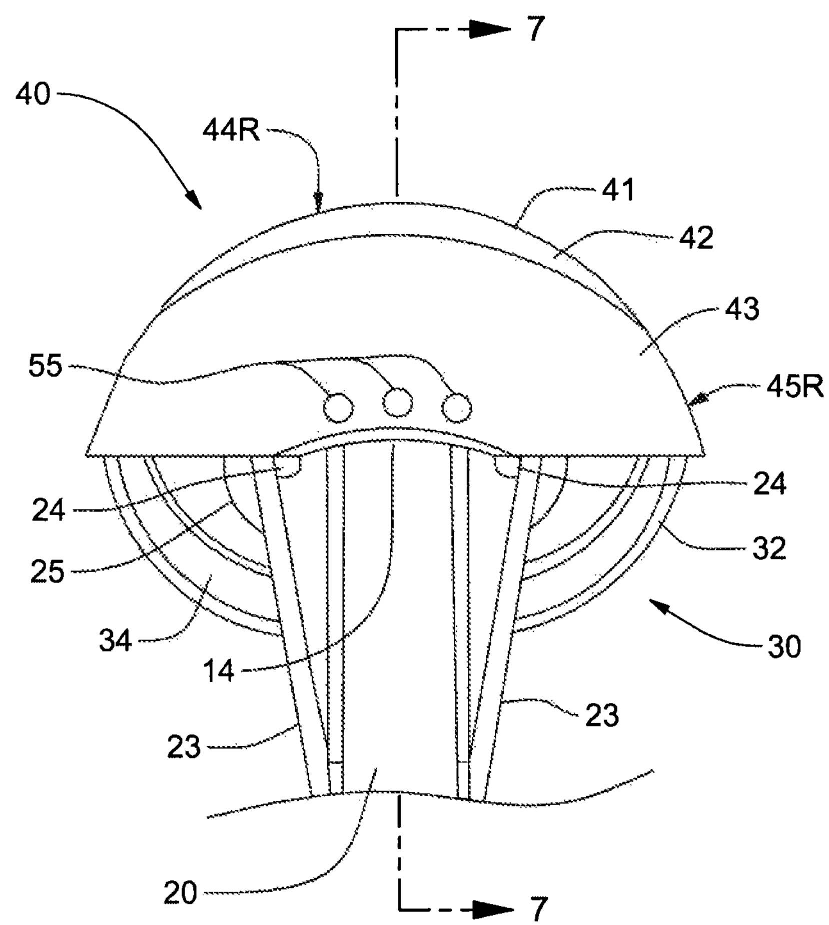
FIG. 6 is a lateral elevational view of the proximal end of the stem coupled to a humeral head augment device, in accordance with an aspect of the present invention.

FIG. 6 shows the distal, lateral aspect of humeral head augment device 40. Positioned along the distal peripheral edge of humeral head augment device 40 may be at least one hole 55 that the operating surgeon may use for soft tissue attachment purposes. It should be understood to those skilled in the art that several holes may be located along the anterior, posterior and lateral peripheral edge providing various locations for soft-tissue securement.

As seen in FIGS. 7A-7D, humeral head augment device 40 includes an internal surface 46 that has a medial aspect 47 and a lateral aspect 48. When humeral head augment device 40 is operably positioned within shoulder prosthesis 10, medial aspect 47 typically contacts or is proximate with the superior surface of proximal end 14. Extending from medial aspect 47 is at least one locking mechanism 52 that is received by an associated at least one locking mechanism 53. Locking mechanisms 52, 53 act together as a coupling mechanism 54 to secure or couple humeral head augment device 40 to proximal end 14 of stem 20. FIG. 1 depicts the placement of humeral head augment device 40 as being generally lateral to longitudinal axis 16. As a result of the modularity of humeral head augment device 40 relative to stem 20, humeral head augment device 40 may also be placed in other operable positions relative to longitudinal axis 16 depending upon the clinical needs of the patient and resulting intraoperative assessment, including being positioned neutral, medial anterior or posterior to longitudinal axis 16.

Figure 7A:
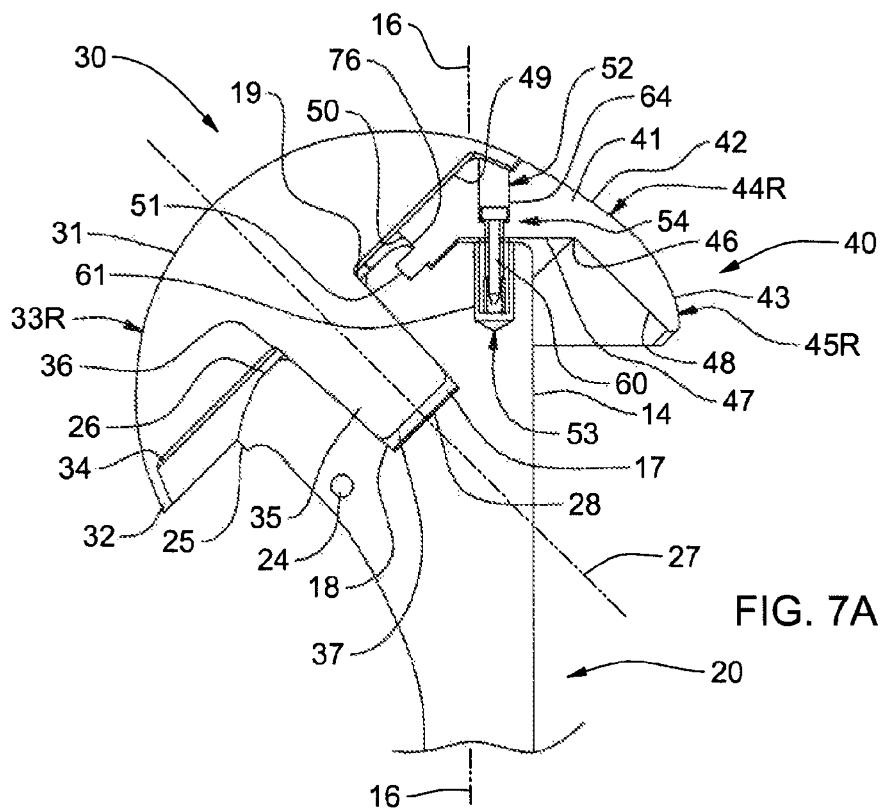
FIG. 7A is a cross-section, side elevational view of the proximal end of the shoulder prosthesis of FIG. 6 taken along line 7-7, showing a locking mechanism of a coupling mechanism configured as an expanding pin, in accordance with an aspect of the present invention.

As shown in the cross-section view in FIG. 7A, locking mechanism 52 includes an expanding screw or pin device 60 extending through a collared cylindrical hole 64 in medial aspect 47. As expanding screw or pin 60 is threaded into receiving cavity 61 of associated locking mechanism 53 that is positioned within proximal end 14, expanding screw or pin device 60 engages receiving cavity 61 resulting in the securement of humeral head augment device 40 to stem 20.

Figure 7B:
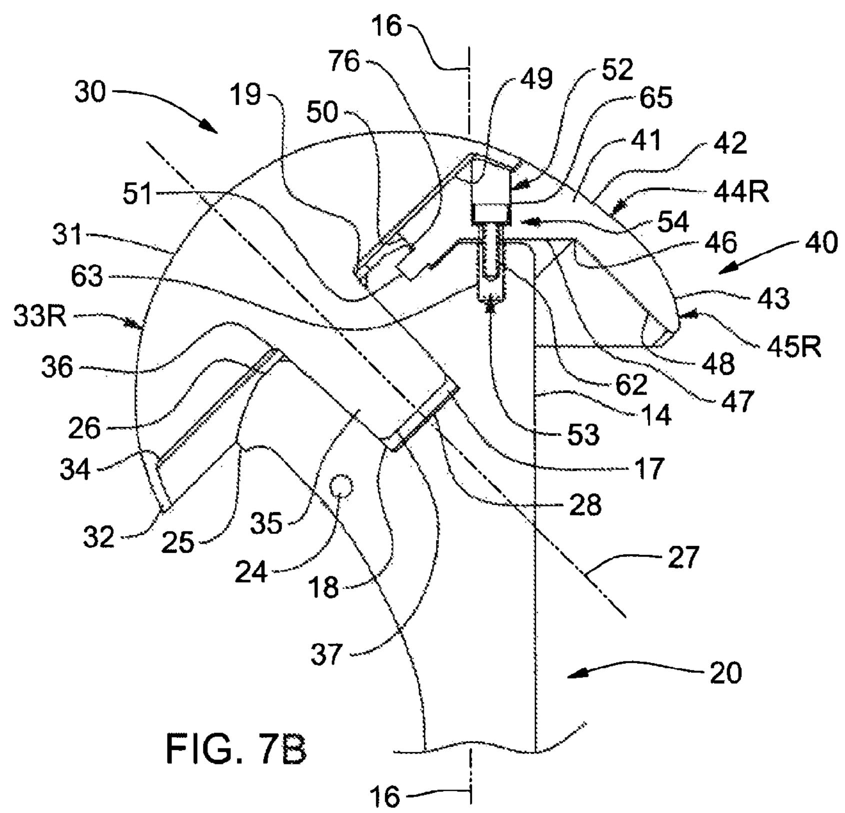
FIG. 7B is a cross-section, side elevational view of the proximal end of the shoulder prosthesis of FIG. 6 taken along line 7-7, showing an alternative locking mechanism of a coupling mechanism configured as a threaded screw, in accordance with an aspect of the present invention.

FIG. 7B is a cross-section view of humeral head augment device 40 that shows an alternative coupling mechanism 54, consisting of a threaded screw 62 and a threaded hole 63. Locking mechanism 52 includes a threaded screw that extends through a collared cylindrical hole 65 in medial aspect 47. Associated locking mechanism 53 consists of threaded hole 63 positioned in proximal end 14. In operation, threaded screw 62 is inserted into the hole and engages the corresponding threads of threaded hole 63 causing humeral head augment device 40 being fixed to stem 20.

Figure 7C:
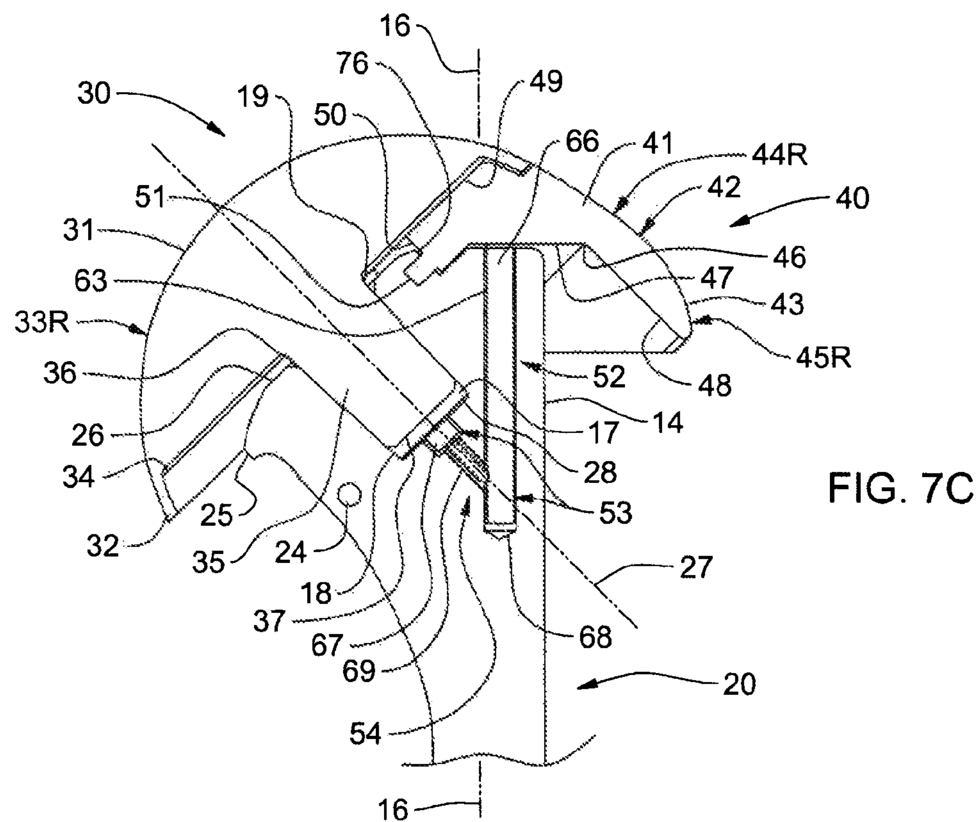
FIG. 7C is a cross-section, side elevational view of the proximal end of the shoulder prosthesis of FIG. 6 taken along line 7-7, showing another alternative locking mechanism of a coupling mechanism configured as a threaded screw and cylindrical post, in accordance with an aspect of the present invention.

A further example of coupling mechanism 54 is shown in a cross-section view of humeral head augment device 40 at FIG. 7C. Locking mechanism 52 consists of at least one cylindrical post 66 extending from medial aspect 47 of internal surface 46. The associated locking mechanism 53 includes a corresponding at least one cylindrical hole 68 configured and dimensioned to receive at least one post 66 and a threaded set screw 67 that is inserted into a threaded hole 69 that projects from cavity bottom 28 of taper cavity 17 and intersects hole 68 at an angle relative to longitudinal axis 16. Alternative coupling mechanism 54 functions by having at least one post 66 fully inserted into at least one hole 68 with medial aspect 47 contacting or being proximate the superior surface of proximal end 14 with threaded set screw 67 being inserted into threaded hole 69 that when fully engaged, threaded set screw 67 pressingly fixates post 66 into hole 68.

Figure 7D:
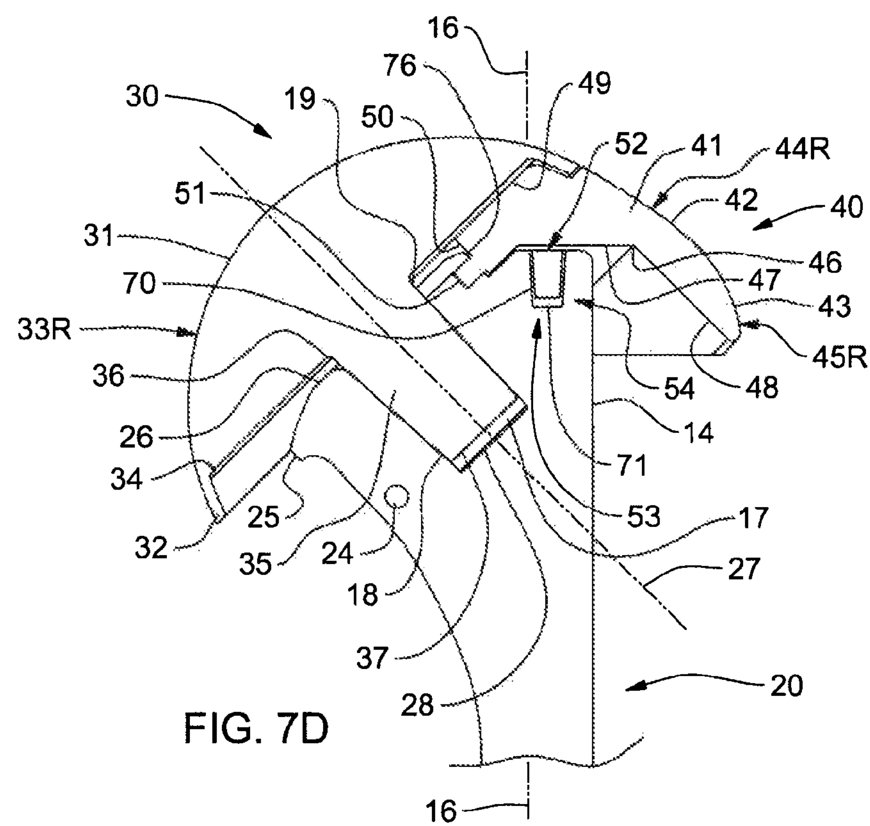
FIG. 7D is a cross-section, side elevational view of the proximal end of the shoulder prosthesis of FIG. 6 taken along line 7-7, showing yet another alternative locking mechanism of a coupling mechanism configured as a male-female locking taper, in accordance with an aspect of the present invention.

Cross-section view of humeral head augment device 40 at FIG. 7D depicts yet a further alternative coupling mechanism 54. Locking mechanism 52 typically includes a male conical taper 70 projecting from medial aspect 47 of internal surface 46. Male conical taper 70 is oriented about normal relative to medial aspect 47. Associated locking mechanism 53 is a female conical taper 71 that is sized and dimensioned to receive male conical taper 70. Female conical taper 71 is positioned within proximal end 14 with a centerline that is almost normal to the superior surface of proximal end 14. In use, alternative coupling mechanism 54 is a taper lock connection formed by the engagement of male conical taper 70 and female conical taper 71 that results in humeral head augment device 40 being secured to stem 20. It should be understood to those skilled in the art that this alternative coupling mechanism 54 may be reversed in that male conical taper 70 could extend from proximal end 14 and female conical taper 71 could be located within medial aspect 47 of humeral head augment device 40.

Figure 7E:
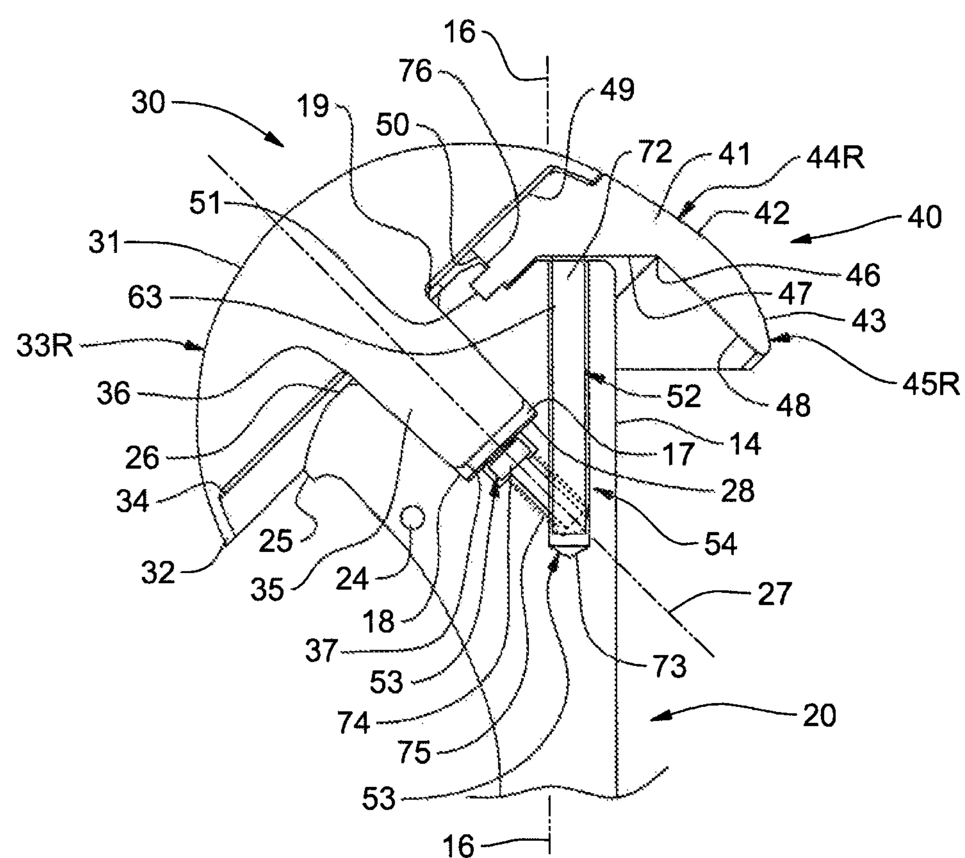
FIG. 7E is a cross-section, side elevational perspective view of the humeral head augment device of FIG. 6 taken along line 7-7, showing a further alternative locking mechanism of a coupling mechanism configured as a threaded screw and dual cylindrical posts, in accordance with an aspect of the present invention.

A cross-sectional view of humeral head augment device 40 showing another example of a coupling mechanism 54 is seen at FIG. 7E. Locking mechanism 52 consists of at least two substantially parallel cylindrical posts 72 extending from medial aspect 47 of internal surface 46. The associated locking mechanism 53 includes at least two substantially parallel cylindrical holes 73 that are generally configured and dimensioned to receive at least two posts 72 and a threaded set screw 74 that is inserted into a threaded hole 75 that projects from cavity bottom 28 of taper cavity 17 and intersects both of the at least two substantially parallel cylindrical holes 73 at an angle relative to longitudinal axis 16. Alternative coupling mechanism 54 functions by typically having at least two posts 72 fully inserted into the at least two holes 73 resulting in medial aspect 47 abutting or being proximate to the superior surface of proximal end 14 with threaded set screw 74 being inserted into threaded hole 75 that when fully engaged, threaded set screw 74 urges posts 72 outwardly, thereby pressingly locking posts 72 within holes 73.

It should be noted that it is further contemplated that each of the above described coupling mechanisms 54 may be utilized to secure humeral head augment device 40 to humeral head 30. Although not shown, it should be understood to those skilled in the art that humeral head augment device 40 may be secured to humeral head 30 utilizing a locking mechanism disposed on the seating surface 49 of humeral head augment device 40 and an associated locking mechanism positioned on interior surface 34 of humeral head 30. Possible locking mechanism may include, but are not limited to interlocking tapers, expanding set pins, extending posts and threaded fixation screws.

Humeral head augment device 40 may also include seating surface 49, an antirotation surface 50 and a motion control member 51. As described above, following the securement of humeral head augment device 40 to stem 20, a properly sized humeral head 30 may be attached to stem 20 utilizing a taper lock arrangement. Following attachment of humeral head 30 to stem 20, seating surface 49 will typically abut or be positioned proximate to interior surface 34. Located between seating surface 49 and medial aspect 47 of internal surface 46 is antirotation surface 50. Antirotation surface 50 is oriented substantially perpendicular relative to seating surface 49.

Figure 5A:
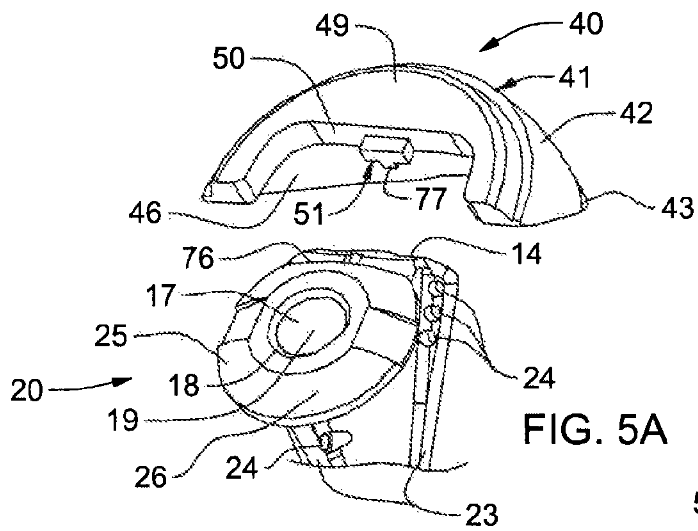
FIG. 5A is a perspective view of the humeral head augment device of FIG. 4, showing a motion control member configured as a rail, prior to being coupled to a proximal end of a stem, in accordance with an aspect of the present invention.
Figure 5B:
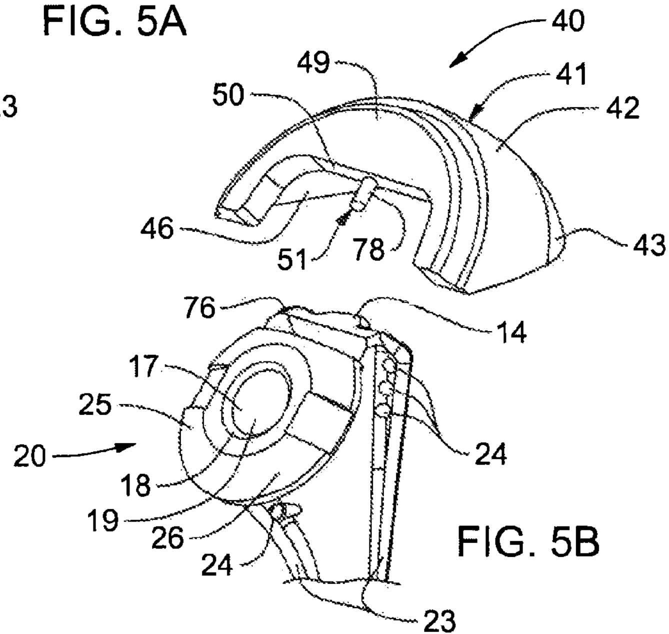
FIG. 5B is a perspective view of the humeral head augment device of FIG. 4, showing an alternative motion control member configured as a pin, prior to being coupled to the proximal end of the stem, in accordance with an aspect of the present invention.
Figure 5C:
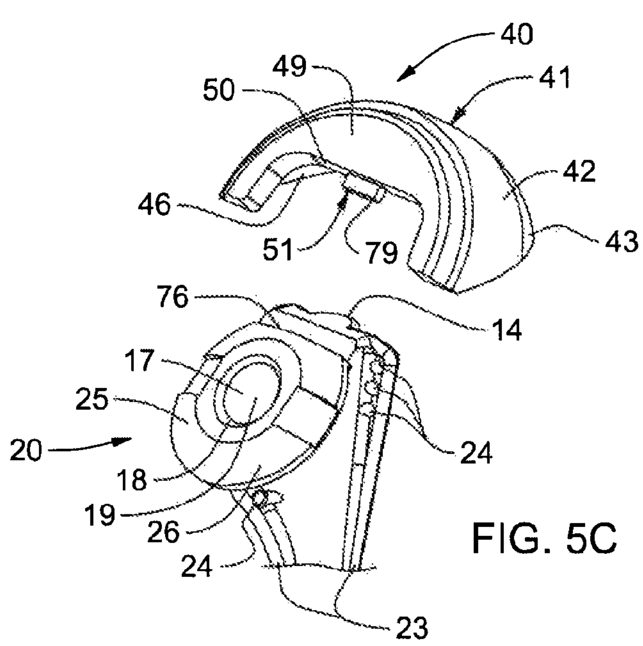
FIG. 5C is a perspective view of the humeral head augment device of FIG. 4, showing an alternative motion control member configured as a tab, prior to being coupled to the proximal end of the stem, in accordance with an aspect of the present invention.

As shown in FIGS. 5A-5C, when humeral head augment device 40 is coupled to proximal end 14, antirotation surface 50 may contact a superior section 76 of collar 25. Extending from the central portion of antirotation surface 50 is motion control member 51.

FIG. 5A depicts one embodiment of motion control member 51 that is generally t-shaped or a "rail" like projection 77 that extends from antirotation surface 50. Superior section 76 of collar 25 has been modified to receive motion control member 51 by including a corresponding cavity or indentation of a similar shape to motion control member 51.

An alternative motion control member 51 is shown in FIG. 5B as a cylindrical post 78 extending from antirotation surface 50. Again, when humeral head augment device 40 is fixed to stem 20, post 78 extends into a corresponding cylindrical hole located on superior section 76.

Yet, a further alternative embodiment of motion control member 51 is seen in FIG. 5C, where motion control member 51 is a rectangular tab 79. Tab 79 projects into a correspondingly shaped cavity located in superior surface 76 when humeral head augment device 40 is coupled to stem 20. It should be understood to those skilled in the art that additional embodiments of the motion control member are contemplated herein, including but not limited to screws, pins, flanges and keys. It is further understood that, all embodiments of motion control member 51 are designed to function to inhibit any rotational or other movement between the coupled humeral head augment device 40 and stem 20. Eliminating or reducing any motion assists to ensure proper positioning of external bearing surface 41 relative to the anatomic bony structures following the implantation of shoulder prosthesis 10 and to humeral head 30.

Figure 8:
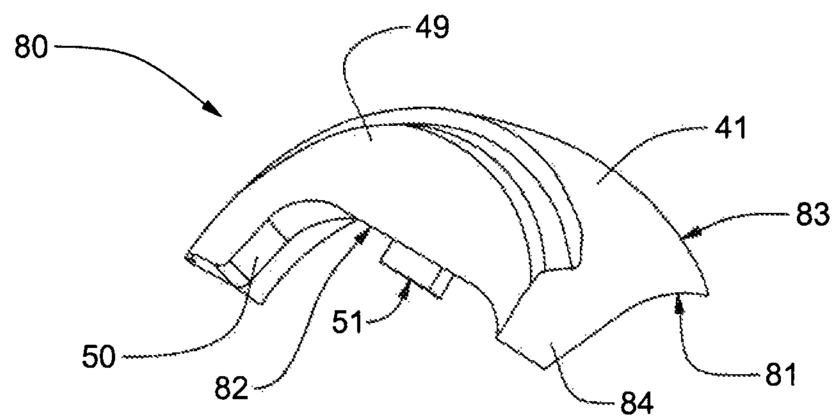
FIG. 8 is a perspective view of an alternative humeral head augment device with a relief disposed on the posterior side extending from the medial side to the lateral side of the alternative humeral head augment device, in accordance with an aspect of the present invention.
Figure 9:
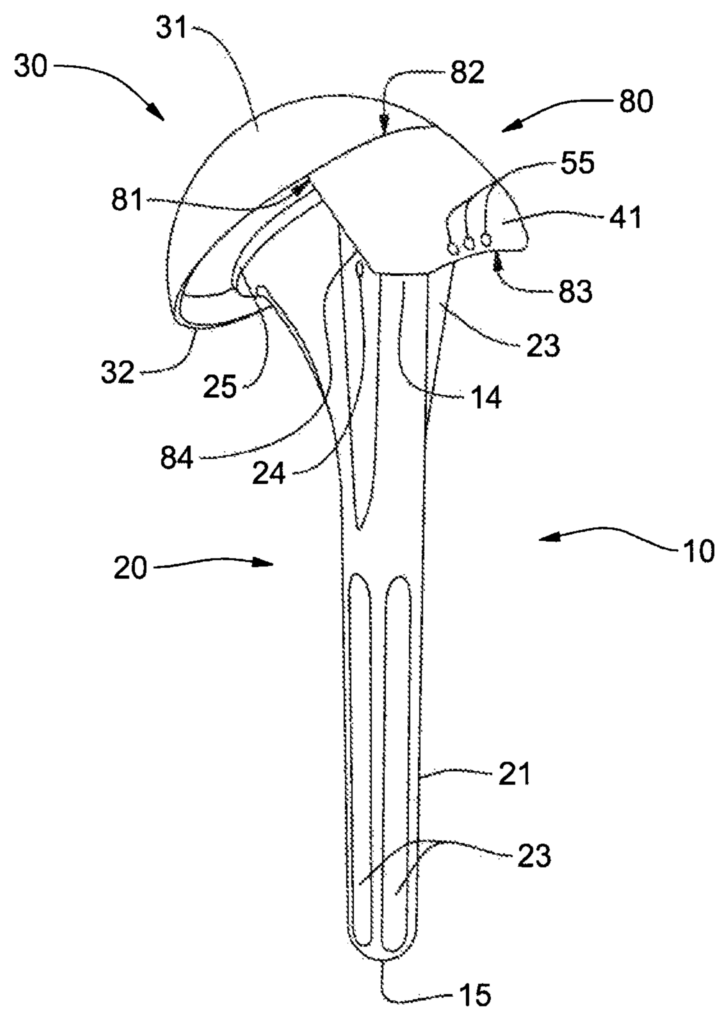
FIG. 9 is a perspective view of a shoulder prosthesis with the alternative humeral head augment device of FIG. 8, coupled in operable position to the proximal end of a stem, in accordance with an aspect of the present invention.

FIG. 8 shows one alternative embodiment of humeral head augment device 80. For some clinical cases, operating surgeons desire to maintain healthy and intact posterior soft tissue structures surrounding the shoulder joint, more specifically, soft tissue structures that comprise the rotator cuff. In these situations, a clinician may choose to utilize alternative humeral head augment device 80. Alternative humeral head augment device 80 includes a unitary body that has a posterior side 81, a medial side 82 and a lateral side 83. To accommodate the posterior soft tissue of the rotator cuff structure, external bearing surface 41 disposed on posterior side 81 is partially relieved or may be totally removed. The resultant relief 84 may extend from medial side 82 to lateral side 83. Alternatively, although not shown, relief 84 may extend only for a portion of posterior side 81 with relief originating either proximate to medial side 82 or proximate to lateral side 83. The remaining portions of external bearing surface 41 remaining intact. Relief 84 will not compromise or impact any of the articulation functionality of external bearing surface 41 that has been described herein. As seen in FIG. 9, alternative humeral head augment device 80 attaches to proximal end 14 in the same manner as has been described previously and is operably positioned in the same location on stem 20 as detailed above, allowing alternative humeral head augment device 80 to interface and function with humeral head 30 in the same or similar way as described for humeral head augment device 40 herein. Further, at least one hole 55 may be positioned along the distal, lateral or anterior aspect of humeral head augment device 80 to facilitate soft tissue securement at various locations along the peripheral rim.

The embodiment of shoulder prosthesis 10 described herein may be modular in design, thereby allowing the operating surgeon to choose from a system of multiple differently sized and shaped components, including stems 20, humeral heads 30 and humeral head augment devices 40. The shoulder prosthesis system provides the operating surgeon with the flexibility to mix, match, and implant the appropriate sized and configured shoulder prosthesis to the presented anatomic structures. The system typically is comprised of a series or plurality of stems comprised of various lengths and cross-sectional sizes. Each stem having a proximal end 14 that may be connected to humeral head 30 and humeral head augment device 40. The shoulder prosthesis system further includes a plurality of different sized humeral heads 30. Each of humeral heads 30 may have a different sized radius of curvature 33R for the respected articulation surface 31. Having a plurality of differing sized and curved humeral heads 30 allows the operating surgeon the ability to more closely match humeral head 30 with the articulating surface of a natural glenoid or a prosthetic glenoid. Each of the plurality of humeral heads 30 will typically include tapered post 35 or another like connector. Additionally, the shoulder prosthesis system will have a plurality of humeral head augment devices 40. Again, the plurality of humeral head augment devices 40 gives the operating surgeon the ability to reestablish shoulder joint stability and provide pain relief without compromising post-operative limb range of motion. Each of the plurality of humeral head augment devices 40 will include the structural features which have been discussed previously herein. The plurality of humeral head augment devices 40 in the system may each have the same or different sized radius of curvatures 44R, 45R for the respected first portion 42 and second portion 43 of external bearing surface 41, and with respect to humeral head 30, radius of curvatures 44R, 45R may be the same or different sized as compared to radius of curvature 33R, thereby allowing the operating surgeon the ability to customize shoulder prosthesis 10 intraoperatively to address motion control, joint stability and soft-tissue deficiencies. Each of the plurality of humeral head augment devices 40 may include a coupling mechanism 54 to allow for securement to one of the plurality of stems 20 in the system and a motion control member 51 that ensures proper alignment of humeral head augment device 40 relative to humeral head 30 and stem 20.

Figure 10:
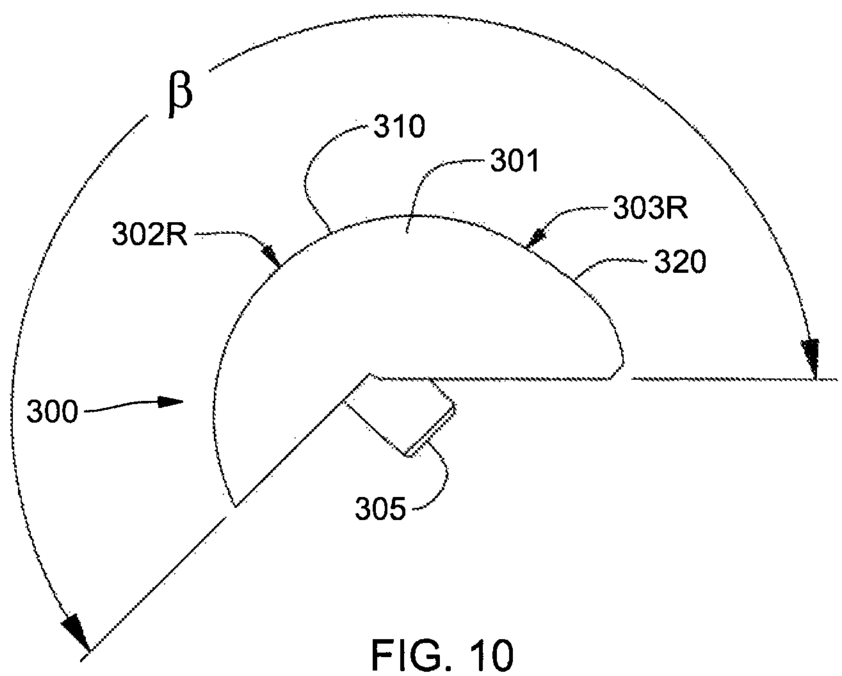
FIG. 10 is a side elevational view of an alternate embodiment of a humeral head augment device, wherein the device is a one-piece humeral-acromion head, in accordance with an aspect of the present invention.

FIG. 10 shows a further alternative embodiment of the humeral head augment device. A one-piece humeral-acromion head 300 is seen with the humeral head augment device being integral to the humeral head. As depicted at FIG. 10, humeral-acromion head 300 includes an outer articulation surface 301. Articulation surface 301 has a generally curved contour that may be comprised of multiple radius of curvatures. It should be understood to those skilled in the art that articulation surface 301 may also be comprised of a single radius of curvature. For example purposes only, FIG. 10 illustrates articulation surface 301 to be comprised of multiple radius of curvatures, 302R, 303R with articulation surface 301 extending to an angle β that may range from 180 degrees to 270 degrees depending upon a patient's anatomic features and clinical circumstances. As discussed previously herein for humeral head 30, humeral-acromion head 300 also includes a tapered post 305 that is similar in structure to tapered post 35. For the sake of brevity and redundancy, the specific structural characteristics of tapered post 305 will not be discussed again as they are essentially the same as those of tapered post 35 of humeral head 30. Tapered post 305 does function to couple humeral-acromion head 300 to stem 20.

As seen in FIG. 10, articulation surface 301 may consist of at least two portions, a glenoid bearing portion 310 and an acromion bearing portion 320. When properly coupled to stem 20, glenoid bearing portion 310 is configured to articulate with a glenoid implant or the patient's natural glenoid. Radius of curvature 302R is configured and dimensioned to allow for three degrees of motion for an implanted shoulder prosthesis. In addition, acromion bearing portion 320 is configured to articulate with the patient's natural acromion allowing for multiple degrees of motion. Glenoid bearing portion 310 will have at least one radius of curvature 302R that may range in size from 15 mm to 45 mm with a more detailed range being between 19 mm to 30 mm.

For example purposes only, as seen in FIG. 10, acromion bearing portion 320 includes at least one radius of curvature 303R. It should be understood to those skilled in the art that acromion bearing portion 320 may be constructed of multiple different sized radius of curvatures. Generally, radius of curvature 303R is differently sized than radius of curvature 302R. The specific size relationship between 302R and 303R (e.g., greater than, less than, or equal) will be dependent upon the presented clinical circumstances and the preference of the operating surgeon.

Acromion bearing portion 320 of humeral-acromion head 300 may be configured to include a relief on the posterior side. As has already been described previously herein, the relief is provided to allow for the placement of intact rotator cuff soft tissue structures. Although not shown, the relief may span the entire posterior side or, alternatively, only a portion of the posterior side of acromion bearing portion 320.

It is also further contemplated, and as described previously herein, humeral-acromion head 300 may include at least one hole positioned along the peripheral rim of both the glenoid bearing portion 310 and acromion bearing portion 320. The hole or holes may be positioned and sized to allow for soft tissue attachment to provide for joint stabilization.

Figure 11:
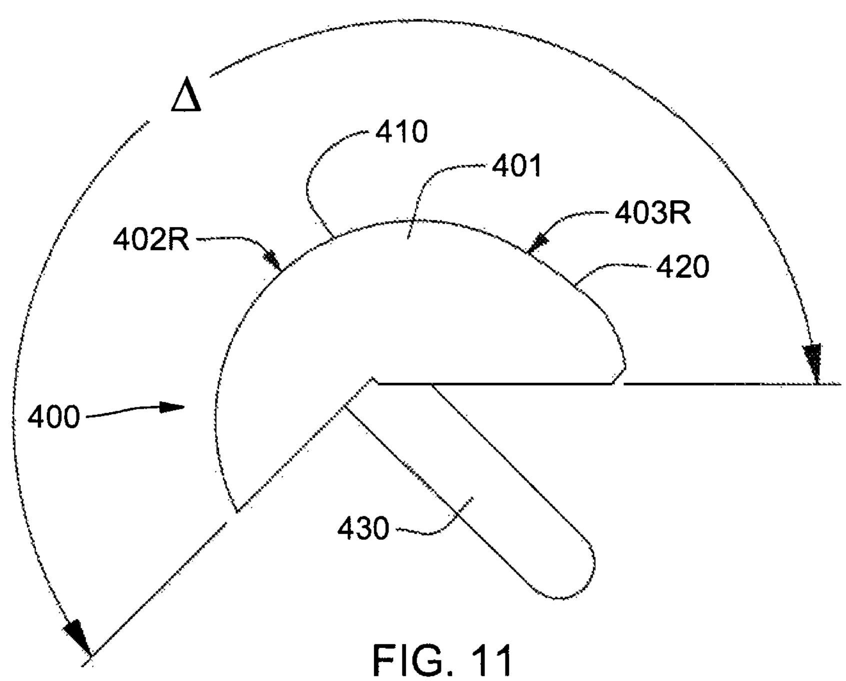
FIG. 11 is a side elevational view of an alternative embodiment of a humeral head augment device, wherein the device is a one-piece humeral-acromion head resurfacing implant, in accordance with an aspect of the present invention.

FIG. 11 shows yet a further alternative embodiment of a humeral head augment device. A humeral-acromion resurfacing implant 400 is seen with the humeral head and the humeral head augment device being a one-piece construct. As shown at FIG. 11, resurfacing implant 400 includes an outer articulation surface 401. Articulation surface 401 has a generally curved contour that may be comprised of multiple radius of curvatures. It should be understood to those skilled in the art that articulation surface 401 may also be comprised of a single radius of curvature. For example purposes only, FIG. 11 illustrates articulation surface 401 to be comprised of multiple radius of curvatures, 402R, 403R with articulation surface 401 extending to an angle Δ that may range from 180 degrees to 270 degrees depending upon a patient's anatomic features and clinical circumstances. Resurfacing implant 400 also includes a tapered post or stem 430 that extends from the undersurface of resurfacing implant 400 and is inserted into the surgically prepared proximal humerus to secure the implanted resurfacing implant 400 to the bone.

As seen in FIG. 11, articulation surface 401 may consist of at least two portions, a glenoid bearing portion 410 and an acromion bearing portion 420. Following implantation, glenoid bearing portion 410 is configured to articulate with a glenoid implant or the patient's natural glenoid. Radius of curvature 402R is configured and dimensioned to and allow for three degrees of motion for an implanted shoulder prosthesis. In addition, acromion bearing portion 420 is configured to articulate with the patient's natural acromion allowing for multiple degrees of motion. Glenoid bearing portion 410 will have at least one radius of curvature 402R that may range in size from 15 mm to 45 mm with a more detailed range being between 19 mm to 30 mm.

For example purposes only, as seen in FIG. 11, acromion bearing portion 410 includes at least one of curvature 403R. It should be understood to those skilled in the art that acromion bearing portion 410 may be constructed of multiple different sized radius of curvatures. Generally, radius of curvature 403R is differently sized (e.g., greater than, less than, or equal) than radius of curvature 402R with the specific size relationship being dependent upon the presented clinical circumstances and preference of the operating surgeon.

Acromion bearing portion 420 of resurfacing implant 400 may be configured to include a relief on the posterior side. As has already been described previously herein, the relief is provided to allow for the placement of intact rotator cuff soft tissue structures. Although not shown, the relief may span the entire posterior side or, alternatively, only a portion of the posterior side of acromion bearing portion 420.

It is also further contemplated, and as described previously herein, resurfacing implant 400 may include at least one hole positioned along the peripheral rim of both the glenoid bearing portion 410 and acromion bearing portion 420. The hole or holes may be positioned and sized to allow for soft tissue attachment to provide for joint stabilization.

The method of assembling shoulder prosthesis 10 includes obtaining a plurality of humeral heads 30 with each humeral head 30 including articulation surface 31, interior surface 34 and a connector for attaching humeral head 30 to stem 20. The method further includes obtaining a plurality of stems 20, each stem 20 having a shaft with a distinct cross-section, a proximal end 14 and distal end 15 with a second connector member for engaging humeral head 30. It is understood that the method includes the step of obtaining a plurality of humeral head augment devices 40 with each of the plurality of humeral head augment devices 40 having external bearing surface 41 with the structural and functionality characteristics described previously herein and coupling mechanism 54. The method may also include the step of assembling one humeral head 30 with one stem 20 and one humeral head augment device 40. Each of these separate components being chosen from the plurality of the respective components contained within a shoulder implant system. The method further includes the steps of employing the coupling mechanism to connect the selected humeral head augment device 40 to the selected stem 20, or alternatively, to the selected humeral head 30. The method may also include the step of engaging the two corresponding connectors of humeral head 30 and stem 20 respectively, resulting in the assembly of shoulder prosthesis 10.

The surgical technique for implantation of a shoulder prosthesis is well known in the art. The method for using a humeral head augment device 40 in a shoulder prosthesis 10 includes, providing a shoulder prosthesis that may include a modular humeral head 30 and a stem 20 that are designed to be coupled to each other by a mechanical coupling mechanism. The method may further include providing a humeral head augment device 40 for attachment to either stem 20 or humeral head 30. Humeral head augment device 40 includes external bearing surface 41 that may include a first portion 42 and second portion 43 with respected radius of curvatures 44R, 45R. Radius of curvatures 44R, 45R may be of different values to constrain translational movement of shoulder prosthesis 10 post-operatively. Humeral head augment device 40 further may include coupling mechanism 54 that is configured to connect humeral head augment device 40 to either stem 20 or humeral head 30. Coupling mechanism 54 allows the operating surgeon to assemble humeral head augment device 40 to stem 20 either prior to implantation into the humerus or following stem 20 being seated into the resected proximal humerus. Humeral head augment device 40 also may include motion control member 51 that maintains accurate orientation of humeral head augment device 40 relative to stem 20 and humeral head 30. Ensuring correct positioning of humeral head augment device 40 relative to the other modular components of shoulder prosthesis 10 will facilitate post-operative joint stability and proper articulation of the humeral head 30 and humeral head augment device 40 with the natural glenoid, a prosthetic glenoid or the natural acromion.

It should be understood by those skilled in the art that the surgical method may include sequentially implanting stem 20 into the prepared proximal aspect of the patient's humerus prior to coupling humeral head augment device 40 to stem 20 or alternatively, to humeral head 30 with the final step being to connect the selected humeral head 30 to stem 20. The sequence of assembly of shoulder prosthesis 10 as described herein may be different depending upon the given clinical situation and whether humeral head augment device 40 is attached to humeral head 30 or stem 20. At the discretion of the operating surgeon, humeral head augment device 40 may be coupled to stem 20 or to humeral head 30 on the "back table" prior to the complete assembly and placement of shoulder prosthesis 10 within the patient's resected humerus. Ultimately, the shoulder prosthesis 10 assembly steps for the method of using a humeral head augment device 40 in shoulder prosthesis 10 and the final sizing combination of stem 20, humeral head 30 and humeral head augment device 40 will vary depending upon the preference of the operating surgeon in combination with the clinical needs of the patient.

Although the preferred embodiments have been depicted and described in detail herein, it will be apparent to those skilled in the relevant art that various modifications, additions and substitutions can be made without departing from its essence and therefore these are to be considered to be within the scope of the following claims.

What is claimed is:

1. A method of manufacturing a shoulder prosthesis, the method comprising:

forming at least one one-piece humeral head, the at least one one-piece humeral head comprising an external articulation surface portion with a radius of curvature, an outer bearing surface portion with at least two radii of curvature, and an inner surface with a first connector extending therefrom; and forming at least one stem, the at least one stem comprising a shaft, a proximal end, and a distal end defining a longitudinal axis therebetween, the proximal end having a second connector configured to engage the first connector of the at least one one-piece humeral head to assemble the shoulder prosthesis, wherein the shoulder prosthesis is configured such that the radius of curvature of the external articulation surface portion extends at least across the longitudinal axis of the stem when the shoulder prosthesis is assembled, wherein the outer bearing surface portion of the at least one one-piece humeral head comprises at least a first bearing surface portion of a first radius of curvature and a second bearing surface portion of a second radius of curvature that is different from the first radius of curvature, the first bearing surface portion being positioned adjacent the external articulation surface portion and the second bearing surface portion being positioned adjacent the first bearing surface portion, and wherein the first radius of curvature of the first bearing surface portion is greater than the radius of curvature of the external articulation surface portion at least immediately adjacent the first bearing surface portion to constrain translation of the shoulder prosthesis when assembled and implanted.

2. The method of claim 1, further comprising engaging the first connector of the at least one one-piece humeral head to the second connector of the at least one stem to assemble the shoulder prosthesis.

3. The method of claim 1, wherein the first radius of curvature of the first bearing surface portion of the at least one one-piece humeral head is greater than the second radius of curvature of the second bearing surface portion of the at least one one-piece humeral head.

4. The method of claim 1, wherein the second radius of curvature of the second bearing surface portion of the at least one one-piece humeral head is greater than the first radius of curvature of the first bearing surface portion of the at least one one-piece humeral head to further constrain translation of the shoulder prosthesis when assembled and implanted.

5. The method of claim 1, wherein the radius of curvature of the external articulation surface portion extends to an angle of at least 180 degrees and from a side of the humeral head.

6. The method of claim 1, wherein the external articulation surface portion encompasses the entire exterior articulation surface of the at least one one-piece humeral head, and wherein the combination of the first bearing surface portion and the second bearing surface encompasses the entire external bearing surface of the at least one one-piece humeral head.

* * * * *